United States Patent
Isaacson et al.

(10) Patent No.: US 10,188,329 B2
(45) Date of Patent: Jan. 29, 2019

(54) SELF-CONTAINED REGIONAL OXIMETRY

(71) Applicant: Nonin Medical, Inc., Plymouth, MN (US)

(72) Inventors: Philip O. Isaacson, Chanhassen, MN (US); Timothy L. Johnson, Plymouth, MN (US); Matthew Prior, Plymouth, MN (US)

(73) Assignee: Nonin Medical, Inc., Plymouth, MN (US)

( * ) Notice: Subject to any disclaimer, the term of this patent is extended or adjusted under 35 U.S.C. 154(b) by 281 days.

(21) Appl. No.: 13/829,158

(22) Filed: Mar. 14, 2013

(65) Prior Publication Data

US 2014/0275885 A1    Sep. 18, 2014

(51) Int. Cl.
*A61B 5/1455* (2006.01)
*A61B 5/00* (2006.01)
*A61B 5/01* (2006.01)

(52) U.S. Cl.
CPC ........ *A61B 5/14552* (2013.01); *A61B 5/0002* (2013.01); *A61B 5/01* (2013.01); *A61B 2560/0431* (2013.01); *A61B 2562/185* (2013.01)

(58) Field of Classification Search
CPC ............ A61B 5/14551; A61B 5/02416; A61B 5/14552; A61B 5/7207; A61B 5/4818
See application file for complete search history.

(56) References Cited

U.S. PATENT DOCUMENTS

| | | |
|---|---|---|
| 5,810,724 A | 9/1998 | Gronvall |
| 6,622,034 B1 | 9/2003 | Gorski et al. |
| 7,671,351 B2 | 3/2010 | Setlak et al. |
| 7,844,315 B2 | 11/2010 | Al-ali |
| 8,301,232 B2 | 10/2012 | Albert et al. |
| 9,693,697 B2 * | 7/2017 | Tal ................... A61B 5/02427 |
| 9,895,090 B2 | 2/2018 | Johnson et al. |
| 2002/0082489 A1 | 6/2002 | Casciani et al. |

(Continued)

FOREIGN PATENT DOCUMENTS

WO    WO-2014/159723 A2    10/2014

OTHER PUBLICATIONS

"International Application Serial No. PCT/US2014/024906, International Search Report dated Sep. 16, 2014", 2 pgs.

(Continued)

*Primary Examiner* — Eric Winakur

(74) *Attorney, Agent, or Firm* — Schwegman Lundberg & Woessner, P.A.

(57) ABSTRACT

A handheld device includes a contact surface, an optical module, a processor, a display module, and a user operable switch. The optical module is disposed on the contact surface. The optical module has at least one optical emitter and at least one optical detector. The at least one optical detector has a light shield associated with the contact surface. The light shield is configured to exclude ambient light from the contact surface when the contact surface abuts tissue of a patient. The processor is coupled to the optical module and configured to execute instructions for determining a measure of oximetry corresponding to the tissue. The display module is coupled to the processor and is configured to indicate the measure of oximetry. The user operable switch is configured to activate at least one of the processor, the optical module, and the display module.

20 Claims, 4 Drawing Sheets

(56) References Cited

U.S. PATENT DOCUMENTS

| | | |
|---|---|---|
| 2002/0116797 A1 | 8/2002 | Modgil et al. |
| 2008/0139908 A1 | 6/2008 | Kurth |
| 2009/0105605 A1 | 4/2009 | Abreu |
| 2009/0163787 A1* | 6/2009 | Mannheimer ...... A61B 5/14552 600/324 |
| 2010/0010326 A1* | 1/2010 | Dalvi ................ A61B 5/14532 600/322 |
| 2010/0125188 A1 | 5/2010 | Schilling et al. |
| 2010/0240972 A1 | 9/2010 | Neal |
| 2010/0312080 A1 | 12/2010 | Isaacson |
| 2010/0331631 A1 | 12/2010 | Maclaughlin |
| 2011/0077473 A1 | 3/2011 | Lisogurski |
| 2011/0224518 A1 | 9/2011 | Tindi et al. |
| 2012/0059267 A1 | 3/2012 | Lamego et al. |
| 2014/0200054 A1 | 7/2014 | Fraden |
| 2015/0099951 A1 | 4/2015 | Al-ali et al. |
| 2015/0141779 A1 | 5/2015 | Johnson et al. |
| 2015/0141780 A1 | 5/2015 | Meyer et al. |

OTHER PUBLICATIONS

"International Application Serial No. PCT/US2014/024906, Written Opinion dated Sep. 16, 2014", 5 pgs.

U.S. Appl. No. 14/082,975, Non Final Office Action dated Aug. 26, 2015, 16 pgs.

Application Serial No. PCT/US2014/024906, International Preliminary Report on Patentability dated Sep. 24, 2015, 7 pgs.

U.S. Appl. No. 14/082,950, Non Final Office Action dated Dec. 16, 2015, 14 pgs.

U.S. Appl. No. 14/082,950, Response filed Jun. 16, 2016 to Non Final Office Action dated Dec. 16, 2015, 11 pgs.

U.S. Appl. No. 14/082,975, Final Office Action dated Mar. 24, 2016, 20 pgs.

U.S. Appl. No. 14/082,975, Response filed Feb. 25, 2016 to Non Final Office Action dated Aug. 26, 2015, 21 pgs.

European Application Serial No. 14775821.3, Response filed May 2, 2016 to Communication pursuant to Rules 161(2) and 162 EPC dated Oct. 22, 2015, 14 pgs.

U.S. Appl. No. 13/829,158 Response filed Jan. 30, 2017 to Final Office Action dated Jul. 18, 2016, 16 pgs.

U.S. Appl. No. 14/082,950 Examiner Interview Summary dated Jun. 22, 2017, 3 pgs.

U.S. Appl. No. 14/082,950 Response filed Feb. 16, 2017 to Advisory Action dated Feb. 8, 2017, 16 pgs.

U.S. Appl. No. 14/082,950, Advisory Action dated Feb. 8, 2017, 3 pgs.

U.S. Appl. No. 14/082,950, Final Office Action dated Aug. 16, 2016, 11 pgs.

U.S. Appl. No. 14/082,950, Non Final Office Action dated Mar. 7, 2017. 13 pgs.

U.S. Appl. No. 14/082,950, Response filed Jan. 17, 2017 to Final Office Action dated Aug. 16, 2016, 13 pgs.

U.S. Appl. No. 14/082,950, Response filed Aug. 7, 2017 to Non Final Office Action dated Mar. 7, 2017, 15 pgs.

U.S. Appl. No. 14/082,975, Final Office Action dated Oct. 14, 2016, 21 pgs.

U.S. Appl. No. 14/082,975, Non Final Office Action dated Jul. 27, 2017, 13 pgs.

U.S. Appl. No. 14/082,975, Response filed Sep. 21, 2016 to Final Office Action dated Mar. 24, 2016, 16 pgs.

U.S. Appl. No. 14/082,975, Response filed Apr. 14, 2017 to Final Office Action dated Oct. 14, 2016, 13 pgs.

European Application Serial No. 14775821.3, Extended European Search Report dated Oct. 18, 2016, 8 pgs.

U.S. Appl. No. 14/082,950, Notice of Allowance dated Oct. 5, 2017, 7 pgs.

U.S. Appl. No. 14/082,975, Final Office Action dated Mar. 20, 2018, 17 pgs.

U.S. Appl. No. 14/082,975, Response filed Dec. 21, 2017 to Non Final Office Action dated Jul. 27, 2017, 11 pgs.

\* cited by examiner

SELF-CONTAINED REGIONAL OXIMETRY

BACKGROUND

A measure of regional oximetry can provide an indication as to tissue health. Existing technology for measuring regional oximetry is inadequate. One example includes an optical sensor coupled by a wire to a processing module. The sensor is held securely to the patient by an adhesive or by a strap encircling the patient.

This arrangement of a sensor and a processor module with a connecting wire is unsatisfactory for certain applications. For example, in an emergency situation or a battlefield environment, the separate nature of the modules and the connecting wire can be inconvenient and may be prone to failure.

OVERVIEW

The present inventors have recognized, among other things, that a problem to be solved can include providing a system for measuring regional oximetry based on a rapidly established temporary coupling to the tissue. The present subject matter can help provide a solution to this problem, such as by a system including a sensor device that can be manually positioned and held briefly at a tissue site and a remote device in wireless communication with the sensor device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
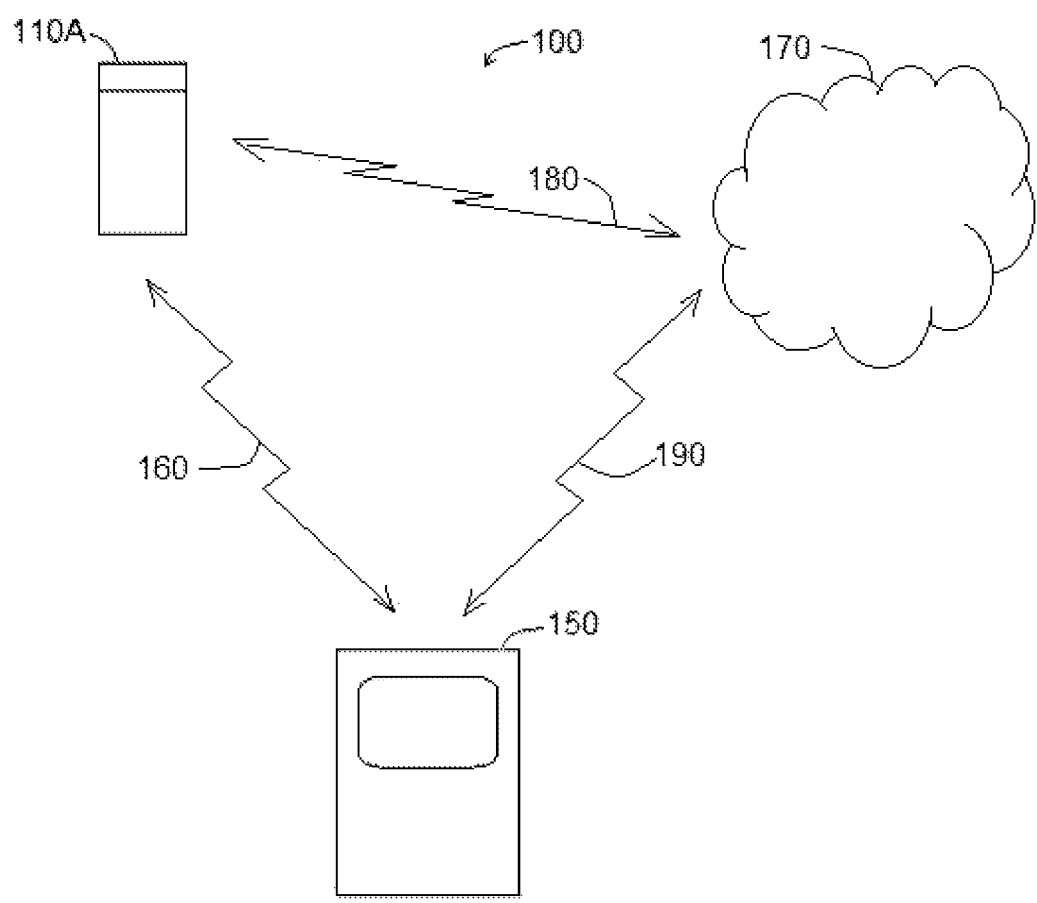
FIG. 1 illustrates a view of a system according to one example.

FIG. 1 illustrates a view of system 100 according to one example. System 100 includes sensor device 110A, remote device 150, and communication network 170.

In one example, sensor device 110A is configured to communicate wirelessly with network 170 by link 180. In addition, sensor device 110A is configured to communicate with remote device 150 by link 160.

Link 160 or 180 can include a communication channel based on symbols carried using a near-field communication channel (such as an inductive coupling) or a far-field radio frequency (RF) channel. In various examples, link 160 or link 180 can include a Bluetooth RF communication channel or an infrared communication channel. Link 160 or link 180 can be bi-directional or uni-directional.

In one example, link 160 includes a wired connection. Remote device 150 can include a docking port that allows physical coupling of sensor device 110A and remote device 150. When physically coupled, sensor device 110A and remote device 150 are able to communicate using link 160. In one example, a docking port is configured for data communication and battery recharging.

Remote device 150 is configured to communicate with network 170 using link 190. In one example, link 190 includes a wired connection to a network device, such as a router, gateway, server, computer or other device. In one example, link 190 includes a wireless communication channel based on symbols carried using an infrared channel or a radio frequency channel. Link 190 can include a Bluetooth RF communication channel. Network 170 can include a local area network or a wide area network, such as the internet.

Sensor device 110A can communicate data and instructions using either or both of link 180 and link 160. In one example, data generated by sensor device 110A is communicated to remote device 150 in real time or in near real time. In other examples, data generated by sensor device 110A is stored until data is requested (pull) or on instruction from sensor device 110A (push). For example, a user can connect sensor device 110A with a docking port of remote device 150A and initiate a routine to download data. This can also include synchronizing or updating of firmware or other programming.

Figure 2:
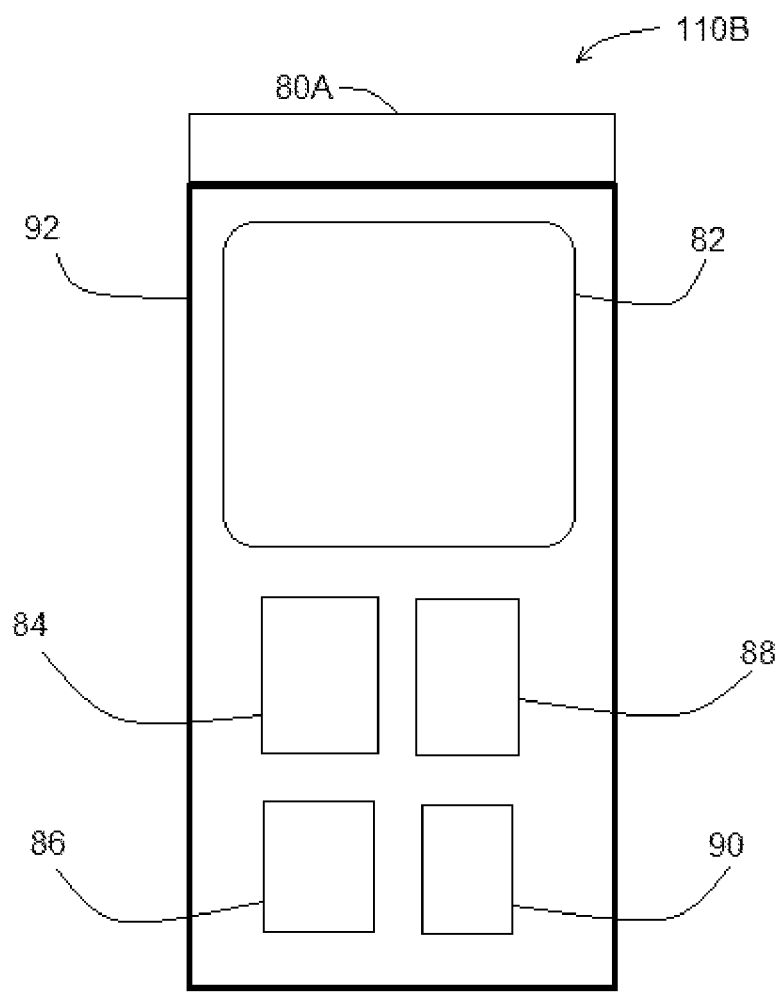
FIG. 2 illustrates a view of a sensor device according to one example.

FIG. 2 illustrates a view of sensor device 110B according to one example. Sensor device 110B, in the example illustrated, includes sensor element 80A, housing 92, interface 82, power module 84, communication module 88, memory 86, and processor 90.

Sensor element 80A includes one or more sensors configured to generate a signal corresponding to a measured parameter. The measured parameter can include a physiological parameter such as oxygenation of tissue or other parameter, some of which are described elsewhere in this document. Sensor element 80A, in the example shown, is at least partially located on a surface of housing 92 and is configured to contact tissue under test.

Housing 92 can include a plastic structure to carry elements, modules, and other components, some of which are described herein. Housing 92 is configured for portability and in one example, has a handle portion suited for manipulation by a user. Housing 92 can include a rigid plastic and some components can be fabricated of soft rubber or silicone. In one example, housing 92 is suited to allow sensor device 110B to be used for single-handed oximety measurement. In various examples, housing 92 is ruggedized for military applications. In one example, housing 92 is waterproof. In one example, housing 92 includes a strap or band to allow the device to be affixed to a patient surface for an extended period.

Interface 82 can include any combination of one or more of a display, a keypad, a touch-sensitive screen, or audio components (such as a microphone or speaker). In one example, interface 82 includes a touch-sensitive screen that allows a user to control an operation of sensor device 110B.

Power module 84 can include a battery or other power source. In one example, power module 84 includes a rechargeable battery. Power module 84 can be recharged when connected to a docking station or can be recharged by other means.

Communication module 88 can include circuitry and components to enable communication with other elements shown, for example, in FIG. 1. Communication module 88 can include, among others, an RF transceiver, an inductive communication module, or an infrared communication module.

Memory 86 provides storage for instructions for use by processor 90 or storage for data corresponding to measured parameters. In one example, memory 86 provides storage for patient information or device information. Measured data, raw data, or other data is stored in memory 86 and can be telemetered to a remote device via a docking station, communication module 88, or other means. In one example, memory 86 is a physical device (such as a card or chip) that can be removed by a user without resort to tools.

Processor 90 includes one or more analog or digital processors. Processor 90 can be configured to execute a set of instructions to perform a method such as that described elsewhere in this document. Processor 90 can be configured to control communications with other elements such as those shown in FIG. 1. In addition, processor 90 can monitor or manage a function of power module 84, read and write data to memory 86, control access to stored data, and perform other functions.

Figure 3:
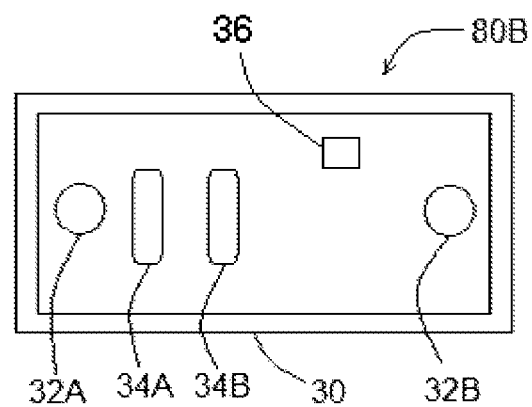
FIG. 3 illustrates a sensor element of a sensor device according to one example.

FIG. 3 illustrates sensor element 80B, according to one example. Sensor element 80B is configured to be accessible on a surface. In one example, sensor element 80B can be manipulated to contact a tissue surface of a patient.

Sensor element 80B, in the example shown, includes detector 32A, emitter 34A, emitter 34B, and detector 32B. Other configurations, including different arrangements of sensors, a different number of sensors, and different types of sensors, are also contemplated. Switch 36, on a surface of sensor element 80B, is configured to detect presence of tissue or contact with tissue.

In the figure, detector 32A, emitter 34A, emitter 34B, and detector 32B are optical elements configured to provide a measure of tissue oxygenation. Tissue oxygenation, sometimes referred to as regional oximetry, can be measured by passing light of a particular wavelength through tissue along pathways having different lengths. In this example, emitter 34A and emitter 34B emit light of a particular wavelength and processor 90 controls their operation. In conjunction with operation of emitter 34A and emitter 34B, detectors 32A and 32B receive light and each provide an electrical output signal. Processor 90 executes instructions to determine tissue oxygenation using the electrical output signals.

Curb 30 is configured as a raised portion about the perimeter of sensor element 80B and provides light shielding. Contaminating light from external sources can affect the light measured by detectors 32A and 32B, and thus impair the accuracy of the tissue oxygenation measurement.

In one example, sensor element 80B includes a flexible membrane that conforms to a patient tissue surface (such as a head or a calf) and provides a good seal to exclude external light. Sensor element 80B can include surface mounted components mounted on a flexible circuit.

In one example, sensor element 80B is permanently affixed to housing 92 and connected to processor 90 by a wired connection. In other examples, sensor element 80B is a field replaceable component and can be affixed to housing 92 without resort to tools or special procedures and element 80B communicates with processor 90 by an electrical connector and socket or by wireless link (near field or far field).

In one example, sensor element 80B is user replaceable in the field. An assortment of different detectors, sensors or components is available. In this way, a user can select a sensor element 80B with optical element characteristics (size, wavelength, and spacing) suited for a particular measurement. For example, a first sensor element 80B can be suited for measurement at a first particular tissue penetration depth and suited for a particular patient size, weight, or age, and a second sensor element 80B can be suited for measurement at a second particular tissue penetration depth and suited for a different particular patient size, weight, or age.

In addition, a user can replace a first sensor element 80B suited for tissue oximetry with a second sensor element 80B suited for pulse oximetry and temperature measurement. Sensor element 80B is encoded with calibration information and other data to allow processor 90 to properly calculate data based on the type of sensor element 80B to which is coupled.

In one example, a program running on processor 90 determines that a different sensor element 80B is connected and a user prompt is provided to solicit entry of identification information for a particular sensor element 80B.

Figure 4:
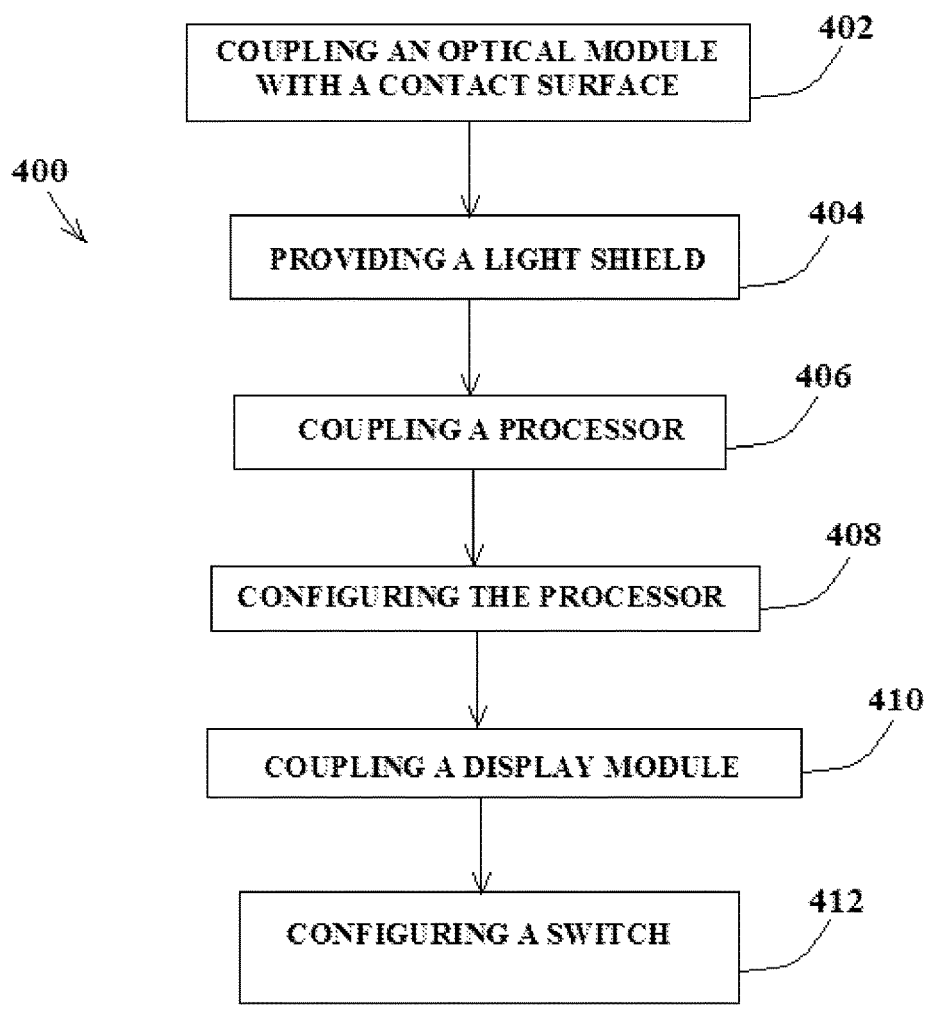
FIG. 4 illustrates a flow chart of a method according to one example.

FIG. 4 illustrates flow chart 400 of a method according to one example. Method 400 relates to fabricating a sensor device.

At 402, an optical module is coupled with a contact surface. The optical module can include one or more light emitters and one or more light detectors. The combination of light emitters and light detectors are configured for tissue oximetry, according to one example. In addition, a light detector and a light emitter maybe configured for pulse oximetry. The optical module can include a light emitting diode and a photodetector.

At 404, a light shield is provided. In one example, the light shield includes a raised curb configured to encircle a photodetector. The light shield can be fabricated of silicone or other compliant material and arranged in a manner to exclude light from the optical module when brought into contact with patient tissue under test.

At 406, the optical module is coupled to a processor. This can include forming an electrical connection. The processor can be coupled to other components as well, including a memory, a processor, an interface, and a switch.

At 408, method 400 includes configuring the processor. This can include providing instructions and data accessible to the processor and configured to implement a routine as described elsewhere in this document. The data can be stored in a memory in the form of a look-up table. A remote module or a remote processor can be electrically connected to the device for downloading executable instructions.

At 410, a display module is coupled to the processor. The display module can include a touch-sensitive screen or interface, such as that shown in FIG. 2 at interface 82.

At 412, a switch is configured to control the device. The switch can include a touch-sensitive switch, a proximity-detecting switch, a manual switch or other type of switch. The switch can be configured to instruct the processor to commence reading and calculating a physiological parameter.

Figure 5:
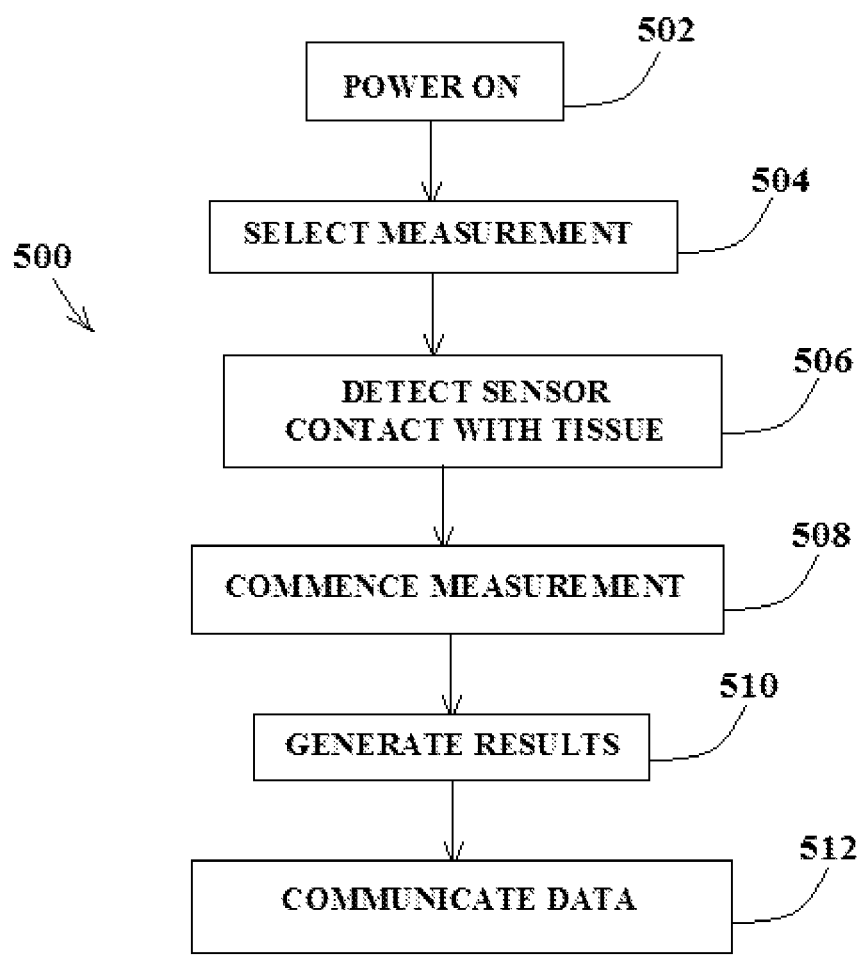
FIG. 5 illustrates a flow chart of a method according to one example.

FIG. 5 illustrates a flow chart of method 500 according to one example. Flow chart 500 relates to measuring a physiological parameter using a device such as that shown in FIG. 2.

At 502, method 500 includes powering on the device. This can include manually actuating an electrical switch to activate a circuit or routine for preparing to take a measurement.

At 504, method 500 includes selecting a measurement to be conducted. The measurement can include determining tissue oximetry ($rSO_2$), temperature, blood pressure, cerebral oximetry, hemoglobin index (HbI), tissue index (TI), pulse strength, pulse oximetry ($SpO_2$), pulse rate, and other measurements.

At 506, method 500 includes detecting contact between the sensor and the patient tissue. This can include detecting contact between sensor element 80B and the patient tissue site. The user can manipulate the device to bring sensor element 80B into physical contact with the tissue. For example, a user-accessible push-button switch can be manipulated and in response to detecting actuation of the switch, processor 90 executes a routine to manage sensor element 80B and generate data as to the physiological parameter.

In one example, touch-sensitive switch 36 is used to detect contact and thus, generate data as to the physiological parameter. Touch-sensitive switch 36 can include a capacitance-based switch. For example, actuation of a capacitance-based switch can be detected as a change in capacitance of a sensor element affixed on sensor element 80B in a manner that responds to tissue contact. As such, when the sensor element is brought into contact with the patient tissue, sensor device 110B detects the tissue and commences a measurement routine. Other types of tissue contact or tissue detection mechanisms are also contemplated. For example, a mechanical switch, an inductive sensor, an optical sensor, a piezoresistive or piezoelectric sensor, can also be used.

At 508, processor 90 commences a routine to collect data used in later processing for determining a physiological parameter. Processor 90 executes instructions upon receiving a trigger signal from having detected contact with the tissue. In one example, this includes executing instructions to energize one or more light emitting diodes and receiving output signals from one or more photodetector in a predetermined sequence. For example, the light emitting diodes and sensors are synchronized in a particular manner in order to avoid interference of one measurement with results from another measurement.

At 510, the results are generated. This can include executing a routine using processor 90 to determine tissue oxygenation or other measurement. In one example, this includes using stored instructions to generate data. The stored instructions can include calibration information. The calibration information can be selected from stored data based on patient identity and patient identity can be captured using a data reader or other means to encode identification data.

At 512, the data is communicated. This can include displaying the data on a user-accessible display (such as interface 82) or communicating the data to a remote device (such as remote device 150 shown in FIG. 1), or a device coupled to network 170 (FIG. 1). In one example, data is communicated using the display and simultaneously (or at another time) communicated using a network link. The data communicated to a network can be either fully processed or encoded in a user-readable form or the data can include raw data corresponding to measured signals and suitable for later processing to derive other data.

Various Notes & Examples

A single-handed regional oximetry measurement device as described herein can be used in an emergency environment, such as an accident scene, a hospital, or on a battlefield.

One example of the present subject matter is battery operated and can used for spot-checking or continuous monitoring of patients in various environments. An example of the device is portable and provides quick and accurate readings of the parameters of interest. To collect data, a user places a sensor module at the tissue site on a patient and the results are generated and displayed in near real-time.

One example includes an LED display and is configured to measure and display the rSO2 and HbI values. The sensing element can include a flexible circuit component and be configured to generate results using two or more wavelengths.

The results can include data to aid in the diagnosis of medical conditions such as diabetes and congenital heart failure. Injury or trauma treatment can be facilitated by a device as described herein. Examples of the device can be used for diagnosing and treating patients suffering a burn, a crush injury, concussion/mild traumatic brain injury, shock, or other hypovolemic states. In addition, such a device can be used for assessing oxygenation of tissue during plastic surgery or vascular surgery. Neonatal screening can also be conducted using an example of the present device. One example includes a housing suited for use in kinesiology applications such as physical therapy and exercise therapy or conditioning work.

Example 1 can include or use subject matter such as a handheld device, and can include or use a contact surface, an optical module, a processor, a display module, and a user operable switch. The optical module can be disposed on the contact surface. The optical module has at least one optical emitter and at least one optical detector. The at least one optical detector has a light shield associated with the contact surface. The light shield is configured to exclude ambient light from the contact surface when the contact surface abuts tissue of a patient. The processor is coupled to the optical module and is configured to execute instructions for determining a measure of oximetry corresponding to the tissue. The display module is coupled to the processor and is configured to indicate the measure of oximetry. The user operable switch is configured to activate at least one of the processor, the optical module, and the display module.

Example 2 can include, or optionally be combined with subject matter of Example 1 to optionally include wherein the user operable switch is coupled to the contact surface.

Example 3 can include, or optionally be combined with subject matter of Example 1 to optionally include wherein the user operable switch is configured to actuate when the tissue is in contact with the contact surface.

Example 4 can include, or optionally be combined with subject matter of Example 1 to optionally include wherein the at least one optical emitter is spaced apart from the at least one optical detector by a distance corresponding to a measure of regional oximetry at a predetermined tissue depth.

Example 5 can include, or optionally be combined with subject matter of Example 1 to optionally include wherein the light shield includes a raised curb.

Example 6 can include, or optionally be combined with subject matter of Example 1 to optionally include a wireless transmitter coupled to the processor, the wireless transmitter configured to telemeter the measure of oximetry to a remote device.

Example 7 can include, or optionally be combined with subject matter of Example 1 to optionally include a pressure sensor coupled to the contact surface and configured to provide a measure of pressure to the processor.

Example 8 can include, or optionally be combined with subject matter of Example 1 to optionally include a temperature sensor coupled to the contact surface and configured to provide a measure of temperature to the processor.

Example 9 can include, or optionally be combined with subject matter of Example 1 to optionally include a handle portion coupled to the contact surface, the handle portion configured for gripping by a user.

Example 10 can include, or optionally be combined with subject matter of Example 1 to optionally include wherein the processor is configured to generate a measure of regional oximetry.

Example 11 can include or use a method including coupling an optical module with a contact surface, providing a light shield for the at least one contact surface, coupling a processor to communicate with the optical module, coupling a display module, and configuring a user operable switch. The optical module has at least one optical emitter and at least one optical detector. The light shield is configured to exclude ambient light from the contact surface when the contact surface abuts tissue of a patient. The method includes configuring the processor to execute instructions for determining a measure of oximetry corresponding to the tissue. The method includes coupling a display module to the processor. The display module is configured to indicate the measure of oximetry. The method includes configuring a user operable switch to activate at least one of the optical module, the processor, and the display module.

Example 12 can include, or can be combined with the subject matter of Example 11 to optionally include wherein configuring the user operable switch includes configuring the switch to actuate when the tissue is in contact with the contact surface.

Example 13 can include, or can be combined with the subject matter of Example 11 to optionally include selecting relative positions of the at least one optical emitter and the at least one optical detector based on a predetermined depth of penetration of light in the tissue.

Example 14 can include, or can be combined with the subject matter of Example 11 to optionally include wherein coupling the optical module with the contact surface includes providing a raised curb.

Example 15 can include, or can be combined with the subject matter of Example 11 to optionally include coupling a wireless transmitter to the processor, the wireless transmitter configured to telemeter the measure of oximetry to a remote device.

Example 16 can include, or can be combined with the subject matter of Example 11 to optionally include configuring a sensor to generate a signal corresponding to blood pressure associated with the tissue.

Example 17 can include, or can be combined with the subject matter of Example 11 to optionally include configuring a sensor to generate a signal corresponding to temperature associated with the tissue.

Example 18 can include, or can be combined with the subject matter of Example 11 to optionally include wherein the processor is configured to generate a measure of regional oximetry.

Example 19 can include or use a system such as can include a housing, a plurality of optical elements, a light shield, and a processing module. The housing has a contact surface and has a handle grip portion. The contact surface is substantially immobile relative to the handle grip portion. The plurality of optical elements is coupled to the contact surface. The light shield is coupled to the contact surface and is configured to exclude ambient light from the plurality of optical elements when the contact surface abuts a tissue surface of a patient. The processing module is configured to determine a measure of tissue oxygenation based on a signal from the plurality of optical elements.

Example 20 can include, or can optionally be combined with the subject matter of Example 1 to optionally include wherein the contact surface is rigidly affixed to the handle grip portion.

Example 21 can include, or can optionally be combined with the subject matter of Example 1 to optionally include wherein the plurality of optical elements includes at least one emitter and at least one detector.

Example 22 can include, or can optionally be combined with the subject matter of Example 1 to optionally include wherein the optical elements are recessed relative to the light shield.

Example 23 can include, or can optionally be combined with the subject matter of Example 1 to optionally include wherein the processing module includes a digital processor.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A handheld device comprising:
  a contact surface coupled to a handle portion, the handle portion configured for gripping by a user;
  an optical module disposed on the contact surface, the optical module having at least one optical emitter and at least one optical detector, the optical module having a light shield associated with a perimeter of the contact surface, the light shield configured to exclude ambient light from the contact surface when the contact surface abuts tissue of a patient, wherein the light shield includes a raised curb;
  a processor coupled to the optical module and configured to execute instructions for determining a measure of oximetry corresponding to the tissue; and
  a display module coupled to the processor and configured to indicate the measure of oximetry; and
  a user operable switch configured to activate at least one of the processor, the optical module, and the display module.

2. The device of claim 1 wherein the user operable switch is coupled to the contact surface.

3. The device of claim 1 wherein the user operable switch is configured to actuate when the tissue is in contact with the contact surface.

4. The device of claim 1 wherein the at least one optical emitter is spaced apart from the at least one optical detector by a distance corresponding to a measure of regional oximetry at a predetermined tissue depth.

5. The device of claim 1 further including a wireless transmitter coupled to the processor, the wireless transmitter configured to telemeter the measure of oximetry to a remote device.

6. The device of claim 1 further including a pressure sensor coupled to the contact surface and configured to provide a measure of pressure to the processor.

7. The device of claim 1 further including a temperature sensor coupled to the contact surface and configured to provide a measure of temperature to the processor.

8. The device of claim 1 wherein the processor is configured to generate a measure of regional oximetry.

9. A method comprising:
  coupling an optical module with a contact surface, the optical module having at least one optical emitter and at least one optical detector and the contact surface coupled to a handle portion, the handle portion configured for gripping by a user;
  providing a light shield at a perimeter of the contact surface, the light shield configured to exclude ambient light from the contact surface when the contact surface abuts tissue of a patient, wherein the light shield includes a raised curb;
  coupling a processor to communicate with the optical module configuring the processor to execute instructions for determining a measure of oximetry corresponding to the tissue;
  coupling a display module to the processor, the display module configured to indicate the measure of oximetry; and
  configuring a user operable switch to activate at least one of the optical module, the processor, and the display module.

10. The method of claim 9 wherein configuring the user operable switch includes configuring the switch to actuate when the tissue is in contact with the contact surface.

11. The method of claim 9 further including selecting relative positions of the at least one optical emitter and the at least one optical detector based on a predetermined depth of penetration of light in the tissue.

12. The method of claim 9 further comprising coupling a wireless transmitter to the processor, the wireless transmitter configured to telemeter the measure of oximetry to a remote device.

13. The method of claim 9 further including configuring a sensor to generate a signal corresponding to blood pressure associated with the tissue.

14. The method of claim 9 further including configuring a sensor to generate a signal corresponding to temperature associated with the tissue.

15. The method of claim 9 wherein the processor is configured to generate a measure of regional oximetry.

16. A system comprising:
  a housing having a contact surface and having a handle grip portion, the contact surface substantially immobile relative to the handle grip portion;
  a plurality of optical elements coupled to the contact surface;
  a light shield coupled to a perimeter of the contact surface and configured to exclude ambient light from the plurality of optical elements when the contact surface abuts a tissue surface of a patient, wherein the light shield includes a raised curb; and
  a processing module configured to determine a measure of tissue oxygenation based on a signal from the plurality of optical elements.

17. The system of claim 16 wherein the contact surface is rigidly affixed to the handle grip portion.

18. The system of claim 16 wherein the plurality of optical elements includes at least one emitter and at least one detector.

19. The system of claim 16 wherein the optical elements are recessed relative to the light shield.

20. The system of claim 16 wherein the processing module includes a digital processor.

* * * * *